US007789602B2

(12) United States Patent
Duesing

(10) Patent No.: US 7,789,602 B2
(45) Date of Patent: Sep. 7, 2010

(54) MOTOR ELEMENT, IN PARTICULAR DENTAL MEDICAL HANDPIECE HAVING A DISCONNECTABLE COUPLING FOR A TOOL-HOLDER

(75) Inventor: Josef Duesing, Leutkirch (DE)

(73) Assignee: Kaltenbach & Voigt GmbH, Biberach (DE)

( * ) Notice: Subject to any disclaimer, the term of this patent is extended or adjusted under 35 U.S.C. 154(b) by 692 days.

(21) Appl. No.: 11/399,261

(22) Filed: Apr. 6, 2006

(65) Prior Publication Data
US 2007/0184407 A1  Aug. 9, 2007

(30) Foreign Application Priority Data
Apr. 7, 2005   (DE) ........................ 10 2005 016 044
Apr. 12, 2005  (DE) ........................ 10 2005 016 870

(51) Int. Cl.
B23B 31/20  (2006.01)
(52) U.S. Cl. ...................... 409/233; 279/46.7; 279/50; 433/129
(58) Field of Classification Search ......... 409/232–234; 403/112, 114, 127, 129; 408/127, 239 R; 279/16, 17, 43, 43.3–43.5, 43.7, 46.1–46.4, 279/46.7, 50–52, 143, 145, 906; B23B 31/20
See application file for complete search history.

(56) References Cited
U.S. PATENT DOCUMENTS

| | | | | |
|---|---|---|---|---|
| 2,898,119 A | | 8/1959 | Hoffmeister ................. 279/51 |
| 4,007,528 A | | 2/1977 | Shea et al. ..................... 32/26 |
| 4,094,521 A | * | 6/1978 | Piotrowski ................. 279/4.09 |
| 4,202,102 A | | 5/1980 | Nakanishi .................... 433/127 |
| 4,334,811 A | * | 6/1982 | Trumpf et al. .............. 409/233 |
| 4,762,447 A | * | 8/1988 | Marantette ................. 409/131 |
| 5,055,044 A | | 10/1991 | Kuhn ........................... 433/126 |
| 5,070,592 A | * | 12/1991 | Sugata ........................ 409/233 |
| 5,609,445 A | | 3/1997 | Dusing ........................ 408/124 |
| 5,730,562 A | * | 3/1998 | Matsumoto et al. ......... 409/233 |
| 5,860,776 A | * | 1/1999 | Sato et al. ................... 409/233 |
| 6,260,855 B1 | * | 7/2001 | Curtis .......................... 279/51 |
| 6,402,442 B2 | * | 6/2002 | Akamatsu et al. .......... 409/134 |
| 6,568,889 B2 | * | 5/2003 | Rohm ......................... 409/233 |
| 6,663,088 B2 | * | 12/2003 | Kimura ..................... 267/64.28 |

(Continued)

FOREIGN PATENT DOCUMENTS

DE  3402585  1/1985

(Continued)

OTHER PUBLICATIONS

European Search Report in DE 10 2005 016 870.1 dated Dec. 22, 2005.

*Primary Examiner*—Eric A Gates
(74) *Attorney, Agent, or Firm*—Marshall, Gerstein & Borun LLP

(57) ABSTRACT

A motor element for a dental medical handpiece or a motor spindle has an elongated shank, rotatably mounted in which there is a drive shaft and a longitudinally-extending rod, a tool-holder for a tool within the rod, and a disconnectable coupling between the rod and the tool-holder. A locking element secures the coupling to prevent the coupling from becoming disconnected from the elongated shank. The locking/unlocking of the coupling is effected by a relative movement between the tool-holder and the tool.

19 Claims, 8 Drawing Sheets

U.S. PATENT DOCUMENTS

| | | | |
|---|---|---|---|
| 6,674,189 B2 * | 1/2004 | Watanabe et al. | 310/52 |
| 7,287,941 B1 * | 10/2007 | Erickson | 409/233 |
| 7,393,311 B1 * | 7/2008 | Giovanelli et al. | 483/1 |
| 2002/0014141 A1 * | 2/2002 | Prust et al. | 82/147 |

FOREIGN PATENT DOCUMENTS

| | | |
|---|---|---|
| GB | 1569843 | 6/1980 |

* cited by examiner

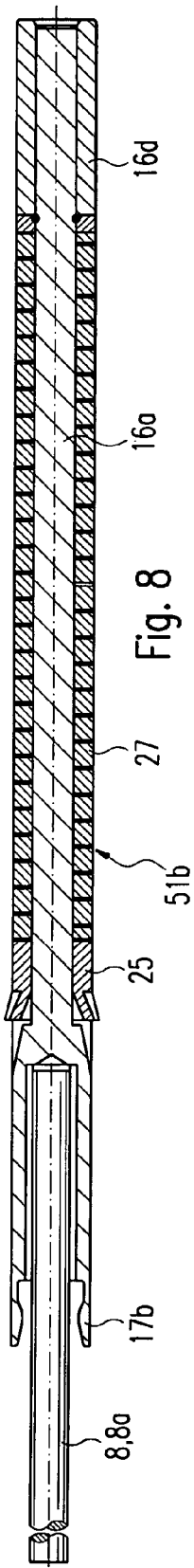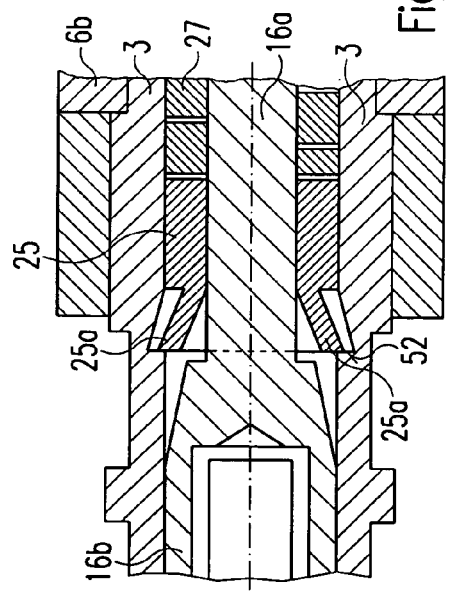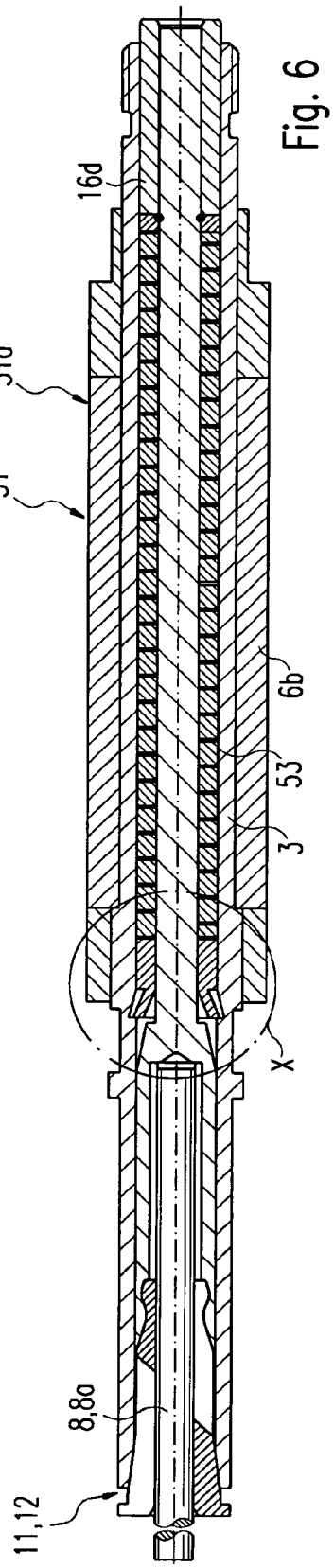

MOTOR ELEMENT, IN PARTICULAR DENTAL MEDICAL HANDPIECE HAVING A DISCONNECTABLE COUPLING FOR A TOOL-HOLDER

BACKGROUND

1. Field of the Invention

The invention relates to a motor element, in particular to a dental medical handpiece.

2. Description of the Related Technology

A handpiece of this kind is described in DE 44 06 855 A1. In the case of this previously known handpiece, a tool-holder that is formed as a collet chuck is pushed into a drive shaft that is formed so that it is hollowly cylindrical at least on the front side, with a coupling for the axial connection of the tool-holder to the drive shaft being formed by a screw coupling. Consequently, the tool-holder is connected to the drive shaft by screwing in and can be disconnected again by unscrewing, in order to clean it for example. This outlay on assembly and disassembly is comparatively great. Moreover, it is mechanically difficult to fix the tool-holder in the screwed-in state in order to avoid unintentional untwisting. It is to be taken into consideration in this connection that during the functional operation of the handpiece when switching the drive shaft on and off torques result that can loosen a screw securing arrangement based on screw-fastening so that the function of the collet chuck can be impeded and impaired without this defect being directly noticeable. A further disadvantage lies in the fact that screw-fastening is comparatively difficult, because the collet chuck is arranged so that it is largely sunk in the drive shaft and it is difficult therefore to reduce a torque for screw-fastening at the front end of the collet chuck.

The underlying object of the invention is therefore to improve the coupling of the tool-holder or the locking and/or unlocking of the coupling in the case of a handpiece in accordance with the invention.

SUMMARY

In the case of a handpiece in accordance with the invention a locking means is formed by a tool in such a way that locking/unlocking is effected by means of a relative displacement between a tool-holder and the tool, with the relative displacement being directed in particular axially and the coupling having a preferably radially movable coupling element. Since in the case of this development the locking means is formed by the tool, the coupling is automatically locked when the tool is introduced into the tool-holder so that no special measure or handling is required for locking purposes. In order to disconnect the coupling it is merely necessary, for example, to draw the tool out of the region of the coupling, whereby the locking is cancelled and the tool-holder can be disassembled.

The development in accordance with the invention is also suitable in a very advantageous way for arranging the axially effective coupling in a drive shaft that is formed so that at least on the front side it is sleeve-shaped or hollowly cylindrically. In this connection, the coupling here as well can be at such a great distance from a front end of the drive shaft that the tool-holder is substantially completely pushed into the hollow drive shaft. In addition, the development in accordance with the invention is also suitable in a very advantageous way for forming the tool-holder by means of a collet chuck. The collet chuck has a plurality of, preferably three, clamping segments, which are arranged so that they lie opposite each other and between which a plug hole for a tool or its shank is provided.

In the case of the development in accordance with the invention, the tool thus has a blocking element which in the plugged-in position of the tool blocks a coupling element of the coupling, moveable between a coupling position and a position of release, in its coupling position. This can be realized in that the movable coupling element in its coupling position is located next to a plug hole and is moved into a free cross section of the plug hole for uncoupling purposes. This can only be effected if the tool is not plugged in. If, on the other hand, the tool is plugged in, the movable coupling element cannot be moved into its position of release, thereby providing the locking in accordance with the invention.

The invention is suitable for a medical handpiece which, depending on the field of use, on the one hand can be of small construction and on the other hand can be of stable construction. A small construction is required for a dental handpiece in order to be able to carry out treatment in the confined mouth space of a patient and in addition to guarantee as well an adequate view of the point of treatment. However, a small construction can also be required for the general medical field, in particular if such a handpiece is to be inserted into small body cavities. The invention is particularly well suited for medical handpieces of stable construction, that is, in particular such handpieces that are used in a medical or dental medical laboratory for working artificial body parts such as prostheses, impressions or casts. Such medical handpieces that have a substantially straight form and a tool-holder, in which a tool with a shank can be plugged into a substantially coaxial position, are termed medically technical or dental medical handpieces or working handpieces in technical terminology. In addition to these medical applications, the tool-holder according to the invention can generally be used in motor elements with a holder for a rotatable tool. A possible application would for example be a high frequency motor spindle.

There is a further advantage of the development in accordance with the invention if the axially effective coupling is formed by a latching arrangement that preferably functions in such a way that when the tool-holder is axially pushed into the plug hole the at least one movable coupling element is moved against an elastic restoring force radially into its position of release and in the axial end coupling position automatically springs into its coupling position. This can be effected, for example, by arranging on the movable coupling element and/or on the counter-coupling element oblique or rounded lead-in faces that give rise to the previously described yielding of the movable coupling element when the tool-holder is plugged in.

In a comparable way it is also advantageous to effect by means of previously described oblique or rounded lead-out faces automatic yielding of the at least one movable coupling element when disconnecting the coupling by axially drawing out the tool-holder. The elastic spring force for moving the coupling element into its coupling position is to be designed and the lead-in faces or lead-out faces respectively are to be designed in each case with such a large angle with regard to the longitudinal axis that the at least one coupling element both when axially plugging in and when axially drawing out with an axial force that can be applied in an operating-friendly manner springs out into its position of release and automatically springs back in.

A development, which can be produced simply and functions in a reliable manner, for the at least one movable coupling element is then achieved if it is arranged on a spring arm that extends from the tool-holder towards the rear. In this connection, the coupling element and the spring arm can be formed as segments and can be separated from the rest of the body of the tool-holder or from at least one adjacent movable coupling element by means of longitudinal slots. If in this case the tool-holder is formed by a collet chuck, it is advantageous for reasons of economy of space to stagger the previously described longitudinal slots for the formation of one or more movable coupling elements with regard to the longitudinal slots of a standard collet chuck in the peripheral direction. Further development features of the invention promote a small construction and ease of production and also functioning.

In accordance with a second aspect of the invention a medical, in particular dental technical or dental medical, handpiece is specified which at least in its front region has an elongated shank, rotatably mounted in which there is a drive shaft which at least in its front end region has the form of a sleeve arranged in which there is a tool-holder which has an axial plug hole for a tool and has clamping segments, formed by longitudinal slots in the tool-holder, with outer cone faces which in cooperation with at least one matching inner cone face in the sleeve give rise, in the event of a longitudinal movement of the tool-holder, to clamping of the clamping segments against the tool that has been plugged into the plug hole, in which case in accordance with the invention it is provided that the outer and inner cone faces are formed so that they converge towards the front, and the rod can be moved towards the front for clamping purposes. These developments do not only render possible simple and spatially favorable constructions, but also relief of the tool-holder in the case of instances of axial overloading directed towards the rear.

Finally, a third aspect relates to a handpiece which at least in its front region has an elongated shank, rotatably mounted in which there is a drive shaft which in its front end region has a tool-holder with a central plug hole and a group of clamping elements that are arranged so that they are distributed over the periphery and can be moved towards the plug hole for a clamping process, with the tool-holder having two groups of clamping elements that are arranged axially one after the other and can be moved simultaneously towards the plug hole. This aspect in turn also relates to a correspondingly configured tool-holder. These developments render possible comparatively stable tool-clamping on account of the axial spacing of two groups of clamping elements that are axially spaced from each other and greater tool-clamping on account of the presence of two coaxially arranged groups of clamping segments, with the clamping and release occurring simultaneously.

BRIEF DESCRIPTION OF THE DRAWINGS

Advantageous developments of the invention are explained in greater detail in the following with the aid of an exemplary embodiment and drawings, in which:

FIG. 6 shows a drive shaft constructional unit in an axial longitudinal section;

FIG. 7 shows the detail marked by X in FIG. 6 in an enlarged sectional representation;

FIG. 8 shows a draw-rod constructional unit in an axial section;

DETAILED DESCRIPTION

Figure 1:
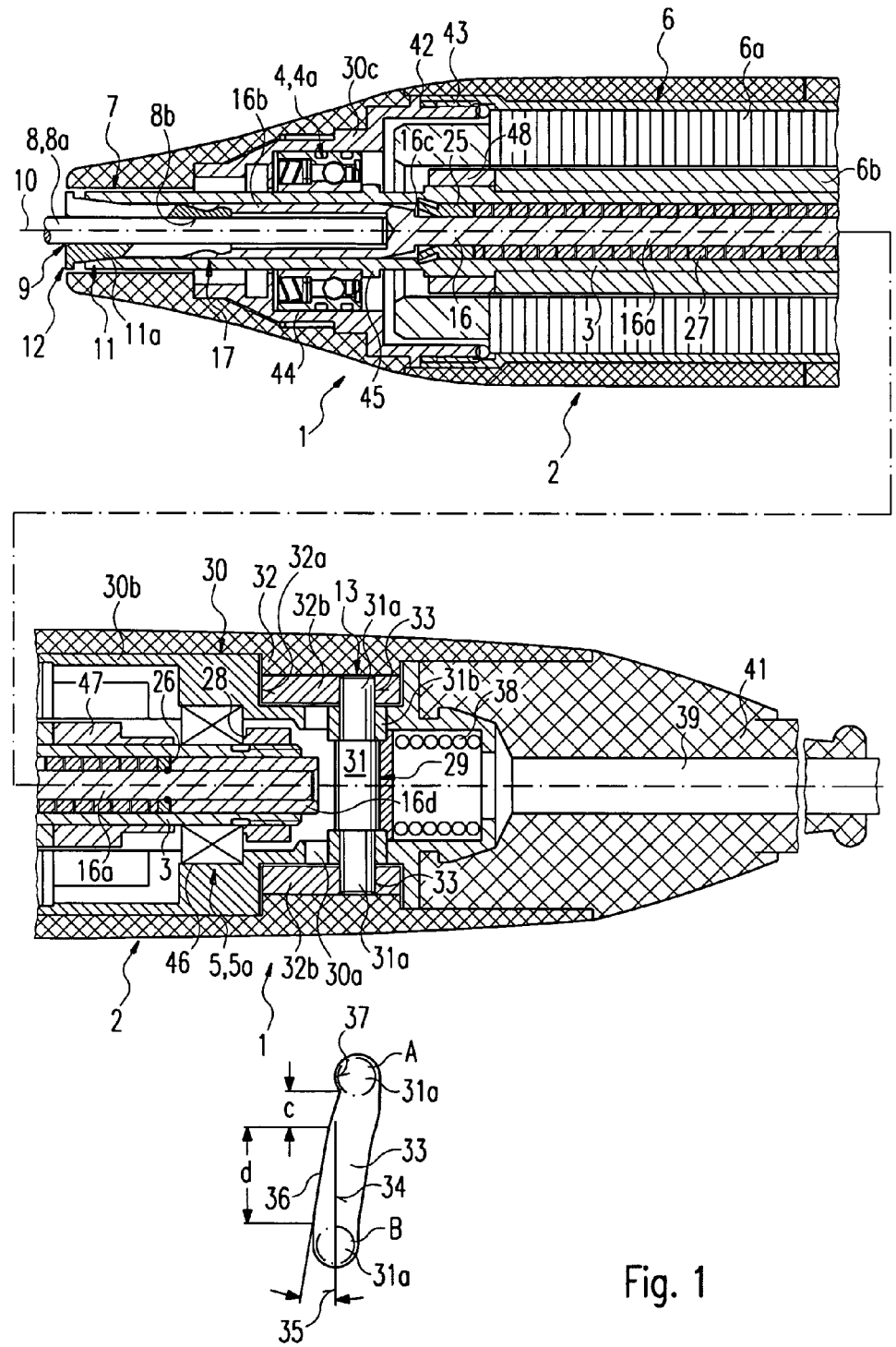
FIG. 1 shows a medical handpiece in accordance with the invention in an axial longitudinal section.

A medical handpiece for a medical or dental laboratory will be described in the following. However, the inventive solution could also be used in other motor elements, for example in motor spindles.

The handpiece denoted in its entirety by 1 is on account of its stable and sufficiently large construction suitable for machining casts, artificial parts such as prostheses, or impressions of the human or animal body. In technical terminology such a handpiece 1 is termed a medical technical or dental technical handpiece or working handpiece. The invention realized is, in principle, suitable for handpieces used for the treatment of teeth in the mouth space of a patient. The same also applies to the medical field.

The main portions of the handpiece 1 are a shank 2 which is used for manual gripping and extends in a straight manner at least in its front region and in the case of the exemplary embodiment extends so that it is straight as a whole, a drive shaft 3 which extends longitudinally in the shank 2 and is mounted in the shank 2 so that it is rotatable in a front and a rear pivot bearing 4, 5 and is axially non-displaceable, a drive motor 6 which is preferably electric and is arranged in the shank 2 as a rotary drive for the drive shaft 3, and a clamping arrangement 7 for a tool 8, shown by way of indication, which can be plugged with a tool shank 8a into a plug hole 9 of the clamping arrangement 7 and can be clamped and can also be disconnected again.

The clamping arrangement 7 has a tool-holder 12 which is preferably formed by a so-called collet chuck 11 which in the case of the exemplary embodiment is mounted in the drive shaft 3 so that it can be displaced in its longitudinal direction and has a plurality of, for example three, clamping segments 11a which are arranged on the end side and so that they are distributed over the periphery and can be clamped by means of a clamping mechanism against the tool 8 or the tool shank 8a and can also be released again by means of a release mechanism 13 that is manually accessible from without. The collet chuck 11 can be longitudinally displaced between a clamping position and a position of release for the clamping and releasing process. In the case of the exemplary embodiment, the clamping segments 11a are preferably compressed radially inwards against the tool 8 or its shank 8a when the collet chuck 11 moves back. A clamping cone 15 with an inner cone 15a in the drive shaft 3 and matching outer cone faces 15b on the clamping segments 11a is used for this purpose. In the position of release of the collet chuck 11 where it is displaced towards the front, the clamping segments 11a are not under any clamping pressure so the tool shank 8a can be plugged into or drawn out of the collet chuck 11. So that the clamping segments 11a are not moved too far radially inwards in the absence of the tool 8, arranged at the front ends of the clamping segments 11a there are flange pieces 11b that limit the movement of the collet chuck 8 axially inwards by butting against the drive shaft 3.

A longitudinally extending rod 16, in the exemplary embodiment in accordance with FIG. 1 a draw rod that is mounted so that it is coaxially displaceable in the drive shaft 3 and is detachably connected at its front end to the rear end of the collet chuck 11, is used to move the collet chuck 11 to and fro in a longitudinally directed manner. To this end, arranged between the rod 16 and the collet chuck 11 there is a coupling 17, which is effective axially and in a form-locking manner, having a first coupling element 17a on the one portion that is to be coupled and a second coupling element 17b on the other portion that is to be coupled, with the first coupling element 17a being moveable between a coupling position where it engages in a form-locking manner behind the other coupling element 17b in an undercut 18 and a position of release where it has moved out of the undercut 18 and being capable of being locked by means of a locking element 8b in the coupling position. As a result of the locking it is guaranteed that the movable coupling element 17a not only engages behind the other coupling element 17b in the coupling position in a form-locking manner, but that it is also locked therein in order to prevent it from moving out. As a result, the coupling security is guaranteed so that the coupling 17 can transmit axial forces from the rod 16 to the collet chuck 11 or vice versa.

The invention is not limited to a tool-holder 12 in the form of a collet chuck 11. Within the scope of the invention a clamping arrangement 7 can be provided, for example, in the front end region of the tool-holder 12 and have, for example, a gripping screw with which a tool can be firmly gripped on the tool-holder. That is why the description continues in the following with reference to the component tool-holder 12, if a collet chuck 11 is not required.

Within the scope of the invention, the radially movable first coupling element 17a can be arranged on the rod 16 and the radially rigid second coupling element 17b can be arranged on the tool-holder 12. In the case of the exemplary embodiment, the reverse arrangement is provided. The first coupling element 17a is arranged on the tool-holder 12 and the second coupling element 17b is arranged on the rod 16. Such a tool-holder 12 has a rear tool-holder section with which it can be plugged into the drive shaft 3, formed so that it is hollow in the front-end region, as far as the region of the coupling 17. A spring element which pretensions the first coupling element 17a into its coupling position where it engages behind preferably automatically effects the movement of the first coupling element 17a into the undercut 17c. In the case of the exemplary embodiment, the first coupling element 17a is arranged on a spring arm 19, which extends towards the rear from the tool-holder body, and protrudes radially outwards from this spring arm 19. The first coupling element 17a and the spring arm 19 are separated from the rest of the body of the tool-holder 12 by means of radial longitudinal slots 21 that open out axially at the associated end.

Figure 5:
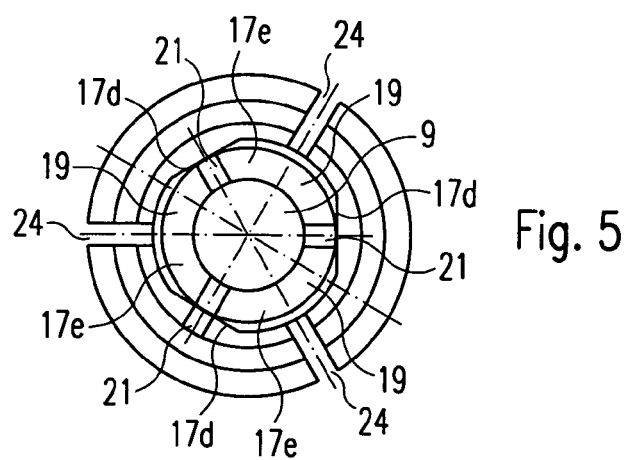
FIG. 5 shows the collet chuck of FIG. 3 in a plan view.

It is advantageous, in order to achieve rotational securement, to form the undercut 17c, which in the case of the exemplary embodiment is provided behind the second coupling element 17b, namely the counter-coupling element, with recessed faces 17d that delimit the first coupling element 17a in both peripheral directions with clearance of motion (FIG. 5). In this respect, rotational securement that is effective in both peripheral directions in a form-locking manner results for the tool-holder 12 in the drive shaft 3. It is, however, also advantageous to form the undercut 17c as an annular groove or as a groove that continues in the clamping segments 11a in the peripheral direction. In such a case, whilst there is no rotational securement in the region of the coupling 17, the advantage that is achieved as a result is that the tool-holder 12 can be pushed into the coupling 17 in any selectable rotational position and can be coupled. Rotational securement can then be realized in a different way. In the case of the formation of the tool-holder 12 as a collet chuck 11, rotational securement is provided by the gripping cone of the collet chuck 11.

In order to facilitate the assembly and/or disassembly of the tool-holder 12, it is advantageous to form the first coupling element 17a and/or the second coupling element 17b with front or rear oblique or rounded lead-in faces 22a, 22b or lead-out faces 23a, 23b respectively which have such a great incline with regard to the longitudinal central axis and rotational axis 10 of the drive shaft 3 that the tool-holder 12 can be pushed into the coupling 17 and/or drawn out of the coupling 17 with an axial force that can be applied in a handling-friendly manner, with the movable coupling element 17a springing out automatically. As a result, a latching arrangement is formed whose latching faces are so large that during the functional operation the axial coupling of the tool-holder 12 is guaranteed and the coupling 17 can be over-pressed, for assembly and/or disassembly of the tool-holder 12, with axial expenditure of force that can be applied manually.

In the case of the exemplary embodiment, in which a plurality of, preferably three, movable first coupling elements 17a with associated second coupling elements 17b with undercuts 17c are arranged so that they are distributed over the periphery, the movable coupling elements 17a are formed with the associated spring arms 19 in each case as identical segments that are arranged on the end side and are separated from each other by means of preferably three longitudinal slots 21 that open out on the end side. The width of the longitudinal slots 21 that is directed in the peripheral direction is so great that the movable coupling elements 17a can spring out in each case, with the existing width of the longitudinal slots 21 thereby being reduced somewhat in each case.

Figure 3:
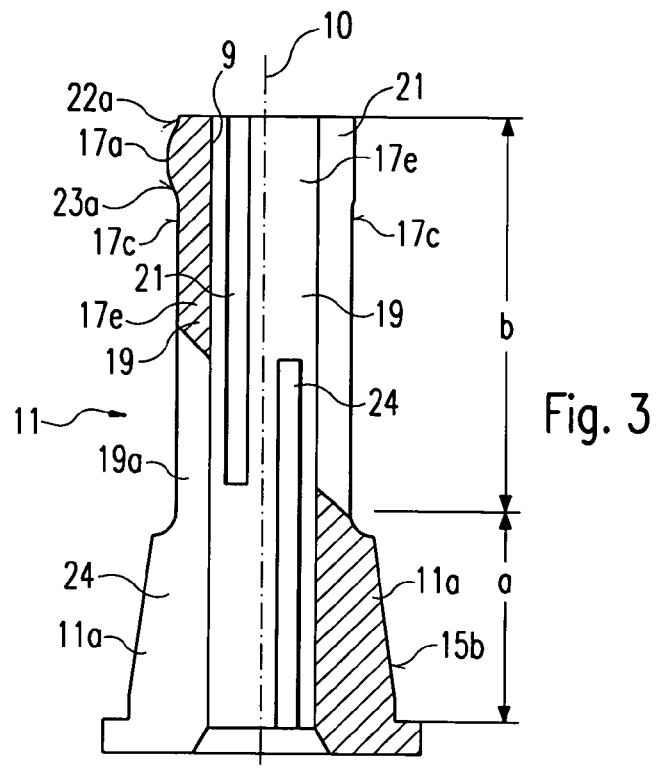
FIG. 3 shows a collet chuck in an axial section.

When the tool-holder 12 is formed as a collet chuck 11 with a plurality of, preferably three, clamping segments 11a, which are arranged so that they are distributed over the periphery, are separated from each other by means of longitudinal slots 24 and are arranged on spring arms 19a formed thereby, in order to reduce the overall length it is advantageous to arrange the longitudinal slots 21 in relation to each other so that they are staggered with regard to the longitudinal slots 24 in the peripheral direction, with it being possible for the longitudinal slots 21, 24 to overlap each other, as clearly shown in FIG. 3.

The sleeve-shaped tool-holder 12 has a hollowly cylindrical plug hole 9, a front conical longitudinal section a and a substantially hollowly cylindrical longitudinal section b extending from the latter towards the rear, the longitudinal sections each being formed by the previously described segments. The cross-sectional shape and size of the plug hole 9 is adapted with little clearance of motion to the cross-sectional shape and size of the tool 8 or tool shank 8a respectively. The wall sections of the preferably hollowly cylindrical plug hole 9 thus form in the region of the clamping segments 11a hollow-cylinder-section-shaped clamping faces and in the region of the coupling segments hollow-cylinder-section-shaped stop faces, with which the coupling elements 17e rest against the peripheral face of the tool 8 or shank 8a respectively.

Figure 2:
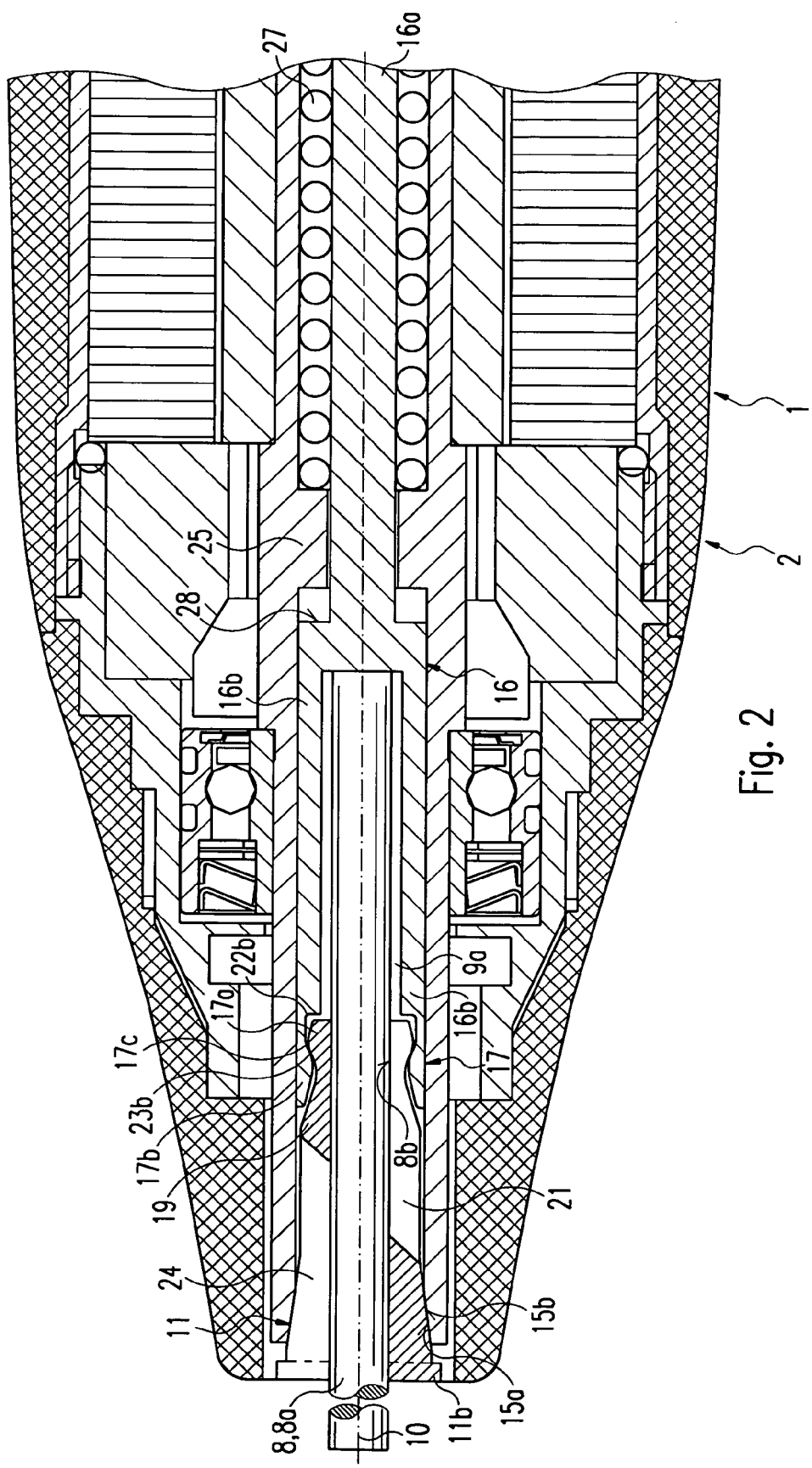
FIG. 2 shows the front end region of the medical hand piece of FIG. 1 in a just slightly modified, enlarged representation.
Figure 4:
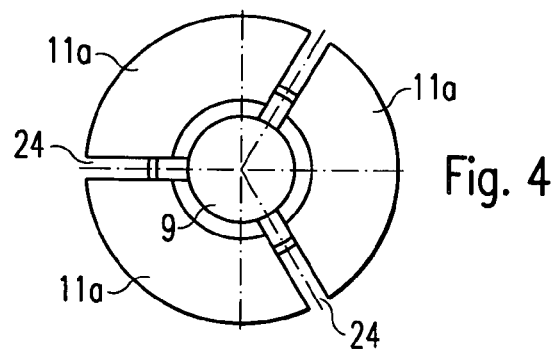
FIG. 4 shows the collet chuck of FIG. 3 in a view from below.

The developments in accordance with FIG. 1 or 2 respectively, on the one hand, and FIG. 5, on the other hand, differ as a result of the lateral surface form of the coupling elements 17e. In accordance with FIG. 1 or 2, the coupling elements 17e are thicker before the associated undercut 17c, with the undercuts 17c being concavely rounded in the longitudinal cross section. In accordance with FIG. 5, the undercut 17c extends from the convex coupling elements 17a substantially cylindrically towards the front.

In the case of the exemplary embodiment, the rod 16 extends from the coupling 17 towards the rear longitudinally through the sleeve-shaped drive shaft 3, preferably projecting thereby over the rear end of the drive shaft 3. Behind the front end region of the rod 16, in which a plug hole 9a is arranged, the rod 16 extends with a rod section 16a that tapers in cross section and is guided in a longitudinally displaceable manner in its front end region in a guide bushing 25 in the drive shaft 3. Located between the rear end of the guide bushing 25 and a shoulder face 26 that is directed towards the front in the rear end region of the rod 16 there is a pressure spring 27 in the form of a helical spring on the tapered rod section 16a pretensioning the rod 16 towards the rear. When the tool-holder 11 is disassembled, the thickened front end region 16b of the rod 16 rests with a rear-side shoulder face 16c against the guide bushing 25. The shoulder face 26 that is arranged on the rear side thereof can be formed by a bushing 16d that is pushed onto the rod section 16a and is fixed thereon and with which the rear end region of the rod 16 is mounted in the sleeve-shaped drive shaft 3 in an axially displaceable manner. The guide bushing 25 in FIG. 2 differs from the other exemplary embodiments in so far as it is formed by an inner ring projection of the drive shaft 3.

In the normal position, the rod 16 which is pretensioned towards the rear by the spring 27 is limited in its movement directed towards the rear in that when a tool 8 is plugged into the collet chuck 11 the outer cone of the collet chuck 11 rests against the inner cone of the drive shaft 3. In order to release the tool 8, the rod 16 is moved forwards by the actuating mechanism 13. This can be effected by means of a pressure element 29 which is formed, for example, as a preferably cylindrical cross pin 31 which can be moved forwards towards the rear end of the rod 16 (portion 16a and/or 16d) by means of the actuating mechanism 13. In the case of the exemplary embodiment, the cross pin 31 is displaceably mounted in the region of its, for example, tapered ends 31a in grooves 33 which are located with a pitch in the peripheral direction of the handpiece 1 in an actuating sleeve 32 which is mounted in an annular groove 32a of the handpiece 1 so that it cannot be displaced axially and so that it is rotatable in the peripheral direction. One of the two grooves 33 is shown by way of example in FIG. 1 as a developed view. The grooves 33, which are preferably arranged in an inner bushing 32b, made in particular from wear-resistant material, for example steel, extend in the peripheral direction in such an oblique or rounded manner that starting from the clamping position shown in FIG. 1 given a relative twist of the actuating sleeve 32 the pressure element 29 is displaced towards the front and thereby moves the rod 16 towards the front and releases the collet chuck 11. In this position of release, the ends 31a of the pressure element 29 are located in the end regions B of the grooves 33. In this connection, the arrangement can be such that the end region B of the grooves 33 that is associated with the position of release is not directed obliquely, but in the peripheral direction so that any automatic untwisting of the actuating sleeve 32 on account of the spring tension and, if applicable, on account of the effect of vibrations is prevented. The incline 36 running obliquely towards the front with regard to an associated transverse plane 35 that is directed at right angles to the longitudinal central axis can vary in the region of the length of the grooves 33. In the case of the exemplary embodiment, starting from the end region A that is associated with the clamping position, a comparatively greatly inclined course of inclination c is provided, following which there is a course of inclination d that is inclined less greatly, following which there is an end region B of the grooves 33 that is directed in the peripheral direction. Provided in the end regions B of the grooves 33, in which the pressure element ends 31a are located in a position that corresponds to the clamping position, there are preferably locating depressions 37 in which the ends 31a can latch and which are directed towards the front in the case of the exemplary embodiment. The pressure element 29 can be pretensioned towards the front and thus also into the locating depressions 37 by means of a spring 38, for example a helical pressure spring, that is arranged behind the pressure element 29. When the actuating sleeve 32 is rotated into the position of release B, the pressure element 29, the rod 16 and the collet chuck 11 are moved forwards into the position of release. When the actuating sleeve 32 is turned back into the clamping position A, the pressure element 29 is moved back again into the distanced clamping position (free position) in which it frees the rod 16, and the collet chuck 11 is clamped on account of the axial spring force that exists.

In the case of the previously described forward and backward movements of the pressure element 29, said element is guided longitudinally, for example by means of sliding sleeves 31b that sit thereon, in longitudinal grooves 30a of a bearing peripheral wall 30b of a handpiece housing 30.

The electric motor 6 is provided as a rotary drive for the drive shaft 3, this being arranged in the handpiece 1 and being arranged, for example, with a sleeve-shaped stator 6a on the inside of the peripheral wall of the existing handpiece housing and sitting with its sleeve-shaped rotor 6b on the drive shaft 3. An electric current line 39, which is shown by way of indication, extends from the rear through a flexible cable bushing 41 made from elastically deformable material which is connected to a rear housing section of the handpiece housing.

The housing 30 consists of two bearing peripheral walls, namely the rear longer peripheral wall 30b and a front shorter peripheral wall 30c that overlap in the front region of the housing 30 and in this region are screwed together by means of an outside thread and an inside thread set therein and adjoin each other at a division joint 42. The screw connection that is arranged, for example, behind the division joint 42 is denoted by 43. The rear peripheral wall 30b is formed so that it is substantially hollowly cylindrical and the stator 6a is arranged in the region thereof. The front handpiece section and the front peripheral wall 30c taper towards the front end of the handpiece 1.

The front pivot bearing 4 is arranged in the front peripheral wall 30c and is formed by a rolling bearing 4a which on the outside sits in a bearing bore 44 that is open towards the rear in the front peripheral wall 30c and on the inside sits on the hollow drive shaft 3, being delimited on the rear side by an annular collar 45 on the drive shaft 3.

The rear pivot bearing 5 is also formed by a rolling bearing which on the outside sits in a bearing bore 46 that is open towards the front in the rear end region of the rear peripheral wall 30b and on the inside sits on the drive shaft 3. The inner ring of the rear rolling bearing 5a is delimited on its front side by the rotor 6b or an intermediate sleeve 47 that rests therein. The rotor 6b is delimited at its front end by an annular collar 48 on the drive shaft 3 which could also be formed by the annular collar 45. Located on the rear side of the rear rolling bearing 5a there is a threaded nut 49 which is screwed from the rear onto a threaded section of the drive shaft 3 and presses the inner ring and also the further ring portions that are arranged on the front side of the latter on the drive shaft 3 against the annular collar 48 and axially fixes them.

In this connection, the drive shaft 3 with the rotor 6b and the rod 16 with the pressure spring 27 form a constructional unit 51 that can be preassembled, see FIG. 6.

In the case of the present exemplary embodiment, this constructional unit 51 consists of two constructional units 51a, 51b, with the constructional unit 51a comprising the drive shaft 3, the rotor 6b, whilst the second constructional unit 51b comprises the rod 16, the bushing 16d, the pressure spring 27 and the guide bushing 25.

One or more shoulder faces 52 that are directed towards the rear and against which the guide bushing 25 is limited in the direction towards the front and positioned are provided in the drive shaft 3 behind the thickened end region 16b for the axial positioning of this constructional unit 51b. The pressure spring 27 is stayed on the rear side on the bushing 16d and it pretensions the guide bushing 25 towards the front, pretensioning the rod 16 towards the rear on account of the axial staying of the guide bushing 25 on the at least one shoulder face 52. In the assembled state, in this case the rod 16 or the bushing 16d is stayed on the rear side on the pressure element 29. This staying can, however, also be effected by delimiting the collet chuck, the clamping segments 11a or the flange pieces 11b on the rear side by means of the drive shaft 3.

In the case of the present exemplary embodiment, the inner constructional unit 51b can be plugged from the front into the hollow drive shaft 3 and be assembled. This is achieved in that the guide bushing 25 has at its front end one or more spring arms 25a which are arranged so that they are distributed over the periphery and the front ends of which in the relaxed state take up a radial measure with regard to the longitudinal central axis 10 that is greater than the radial measure of the receiving hole 53, which is cylindrical preferably over the whole of its length, in the drive shaft. The shoulder face 52 is formed by an annular groove in the receiving hole 53.

In order to install the inner constructional unit 51b in the drive shaft 3, the constructional unit 51b is plugged from the front into the receiving hole 53 until the spring arm or arms 25a, which thereby spring therein, spring out behind the at least one shoulder face 52 and position the constructional unit 51a towards the front at the at least one shoulder face 52.

In the disassembled state, on account of the spring tension of the pressure spring 27 the guide bushing 25 rests against the shoulder face 16c that is arranged in front of it. In the assembled state, on the other hand, between the shoulder face 16c and the guide bushing 25 there is axial clearance of motion even in the clamped state of the clamping segments 11a, that is, in the state in which they have been displaced towards the rear, so the clamping effect of the clamping segments 11a that is directed radially inwards is not impaired.

In order to disassemble the constructional unit 51b, after the tool-holder 9 or the clamping segments 11a has/have been removed, the rod 16 is pushed out towards the rear, with the spring arms 25a springing in without being damaged.

Figure 9:
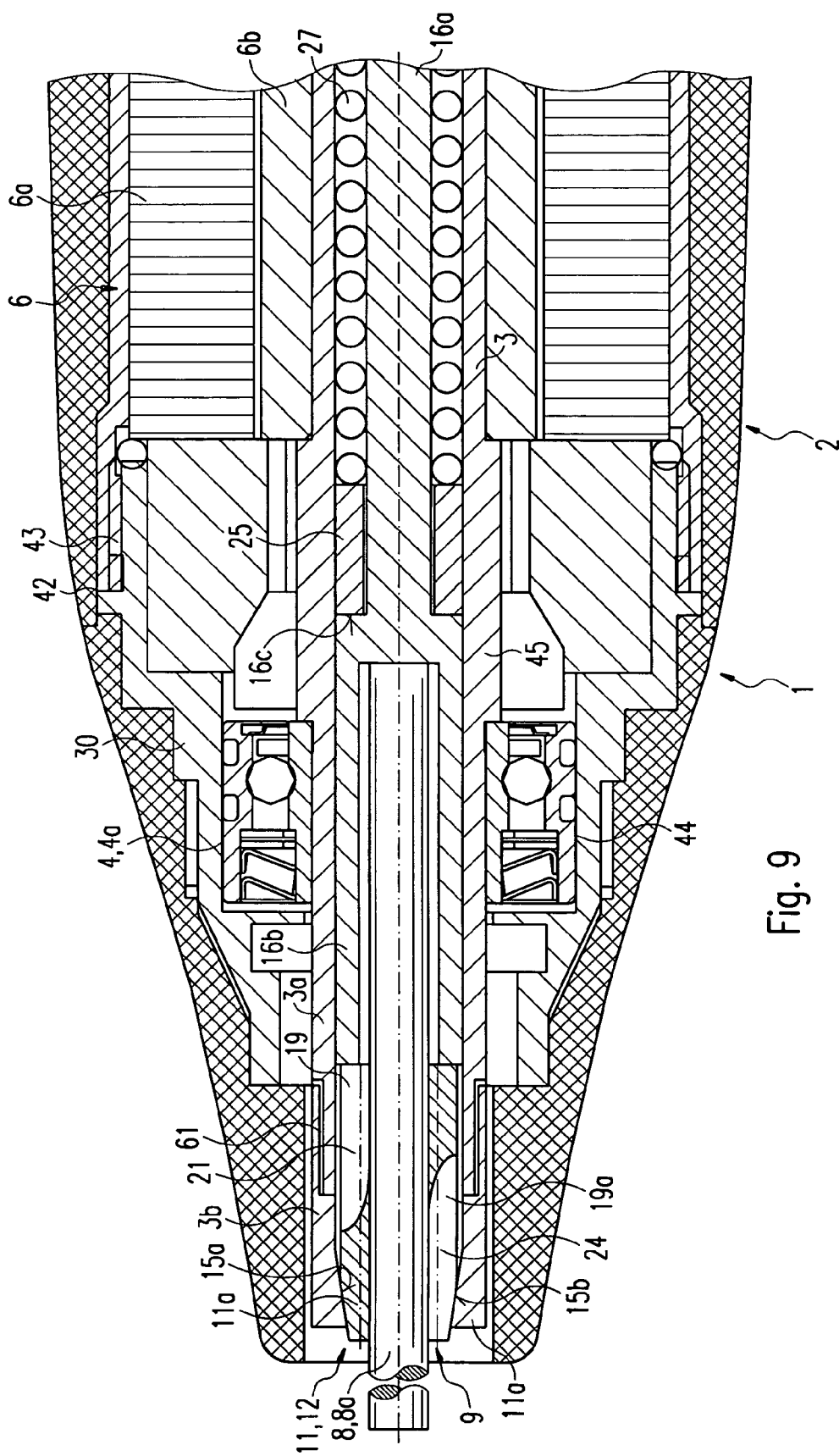
FIG. 9 shows the front end region of a medical handpiece in accordance with the invention in a modified development in an axial longitudinal section.

In the case of the exemplary embodiment in accordance with FIG. 9, in which the same or comparable portions are provided with the same reference numerals, the handpiece 3 has a tool-holder 12 which is formed by a push-out collet chuck 11 that is actuated in that for a clamping process the rod 16 is not drawn back, but is pushed forward and exerts a forwardly directed pressure on the collet chuck. In the case of this development as well, a group of clamping elements formed, for example, by clamping segments 11a with cooperating cone faces are arranged in the tool-holder 12 so that they are distributed around the plug hole 9 and can be moved for a clamping process towards the plug hole 9, although the cone faces, here the inner cone 15a in the drive shaft 3 and the outer cone faces 15b on the clamping segments 11a, are formed so that they converge towards the front and in such a way that they match each other. These cone portions are preferably arranged in the front region of the collet chuck 11.

In the case of this development, no coupling between the collet chuck 11 and the rod 16 is required, since a drawing action does not take place when clamping. The pressure of the rod 16, pressing, for example, obtusely from the rear against the collet chuck 11, in which case no coupling is required, suffices for the clamping function. The collet chuck 11 is held as well in a form-locking manner and so that it is undetachable between the inner cone 15a and the rod 16. In the case of this development as well, the clamping segments 11a are arranged on spring arms 19a which are formed by longitudinal slots 24 that are arranged so that they are distributed over the periphery and open out towards the front. In this connection, longitudinal slots 21 which open out towards the rear can also be provided here, subdividing the collet-chuck body into segments at the rear.

In order to facilitate the assembly of the collet chuck 11, the drive shaft 3, which is formed in a sleeve-shaped manner in this region, is transversely divided behind the inner cone 15a, and the drive-shaft portions 3a, 3b are connected together by means of a releasable connection 61, in particular a screw connection.

In the case of this modified development, the rod 16 is pretensioned by the pressure spring 27 towards the front into its clamping position. The collet chuck 11 is released by a drawing movement of the rod 16 towards the rear that can be generated by the release mechanism 13 moving it towards the rear in opposition to the force of the pressure spring 27.

For this, for example, the grooves 33 can have an opposite pitch so the pressure element 29 is moved towards the rear for the release and draws the rod 16 towards the rear, for example in that the rod 16 engages behind the pressure element 29 and thereby passes through to engage in a hole and engages behind a head portion 16e so that the spring 27 pushes the clamping elements towards the front through the rod 16 and clamps them. In this respect, the push-out collet chuck 11 is effective in an opposite way to that of the draw-in collet chuck 11 in accordance with FIG. 1.

Figure 10:
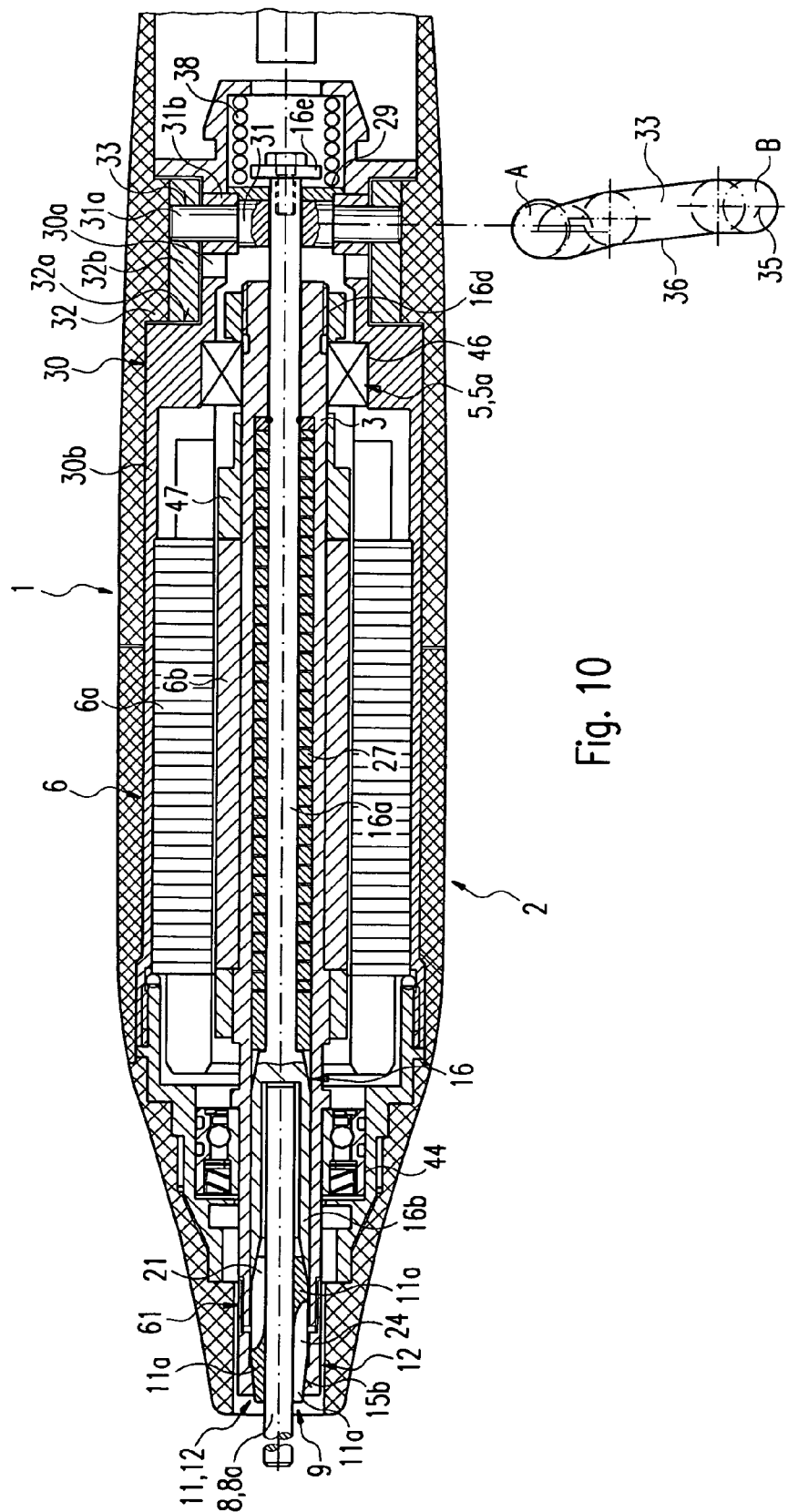
FIG. 10 shows a medical handpiece in accordance with the invention in a further modified development in an axial longitudinal section.

The clamping effect of this tool-holder 12 can be improved in that in accordance with the exemplary embodiment in accordance with FIG. 10 two groups of clamping elements are provided that are arranged axially one after the other and in each case around the plug hole 9 and can be moved towards the plug hole 9. This can be achieved by means of common application of pressure to the groups, that is, in particular in a simple way if arranged in each group there are clamping segments of which the clamping segments 11a of the front group have outer cone faces 15b converging towards the front and those of the rear group have outer cone faces 15b converging towards the rear, with the rod 16 having at its front end a common pressure element which is formed in particular by an inner cone 15c and cooperates with the rear outer cone faces 15b. In this connection, the pressure of the rod 16 acts simultaneously on all the clamping elements.

Figure 11:
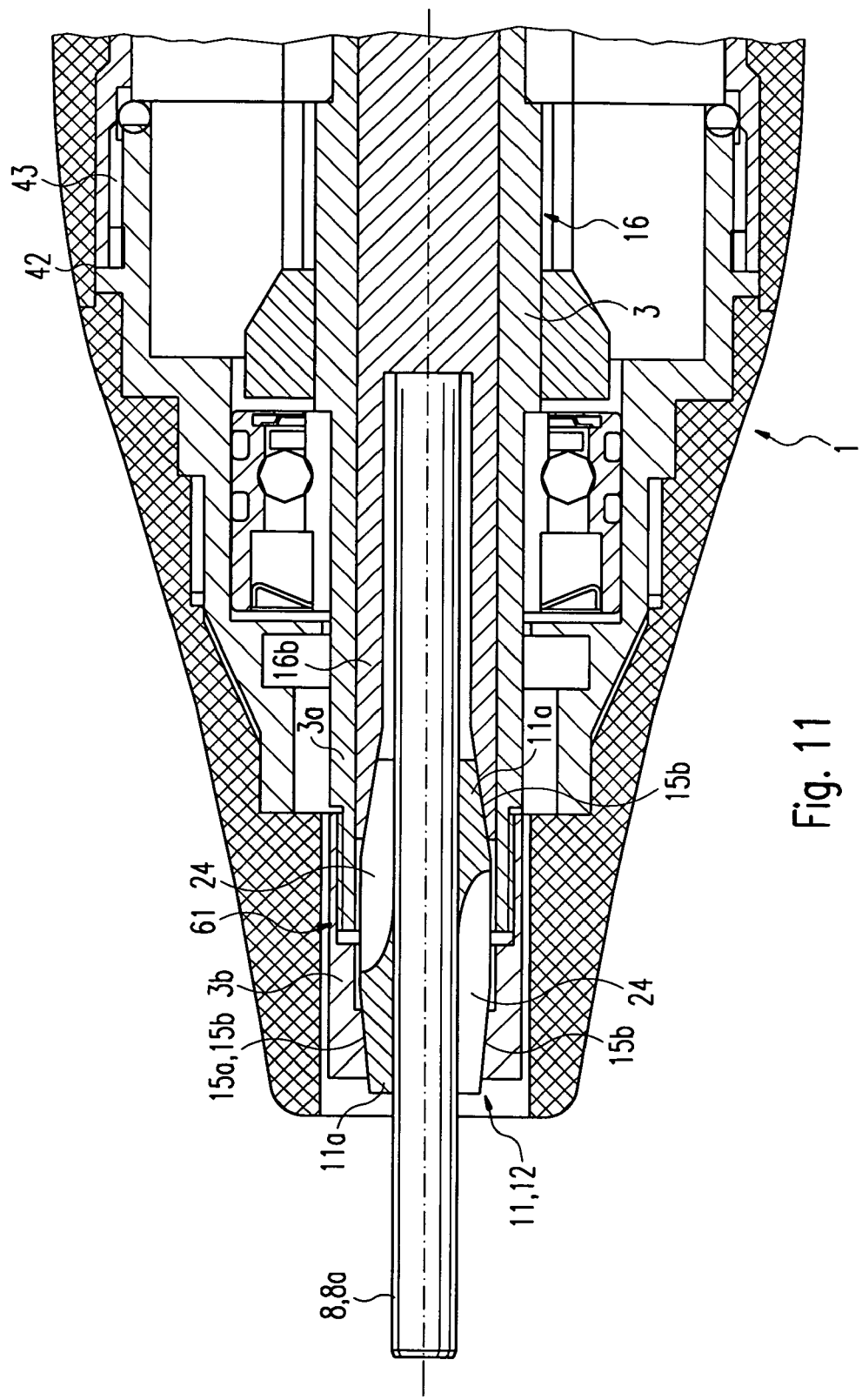
FIG. 11 shows a front end region of the medical handpiece of FIG. 10 in an enlarged representation.
Figure 13:
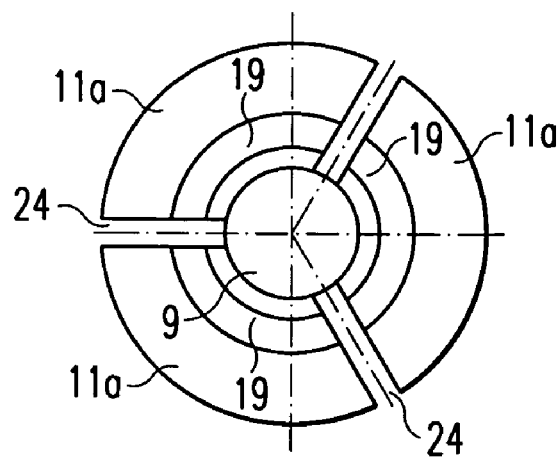
FIG. 13 shows the collet chuck of FIG. 12 in a view from below.
Figure 12:
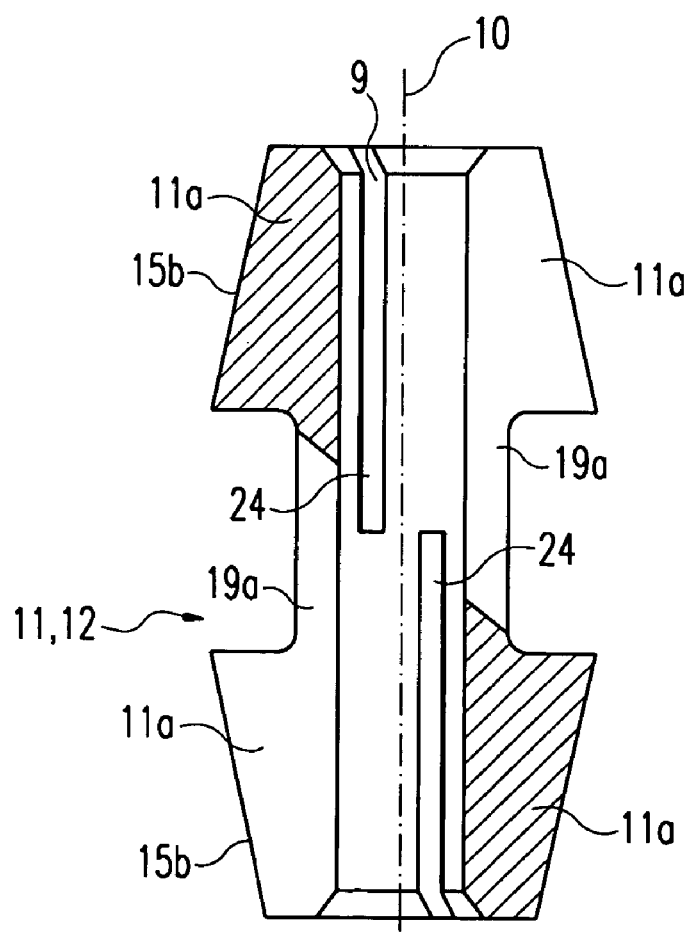
FIG. 12 shows a tool-holder in the form of a collet chuck of the medical handpiece of FIGS. 10 and 11 in an enlarged representation.

As FIGS. 11 and 12 show in particular, in the case of this tool-holder 12 held at both axial ends there is a respective group of, for example, three clamping segments 11a, in each case held on a spring arm 19a and thus capable of moving radially inwards against the spring-arm force. The clamping segments 11a and the spring arms 19a are formed by longitudinal slots 24 in the sleeve body that open out in each case on the end side and therefore guarantee the radial spring path. The longitudinal slots 24 and the clamping segments 11a are preferably arranged so that they are staggered in relation to each other in the peripheral direction. As a result, it is possible to arrange the slots 24 so that they overlap axially, in particular in the central region of the sleeve body and thus in the region between the groups of the clamping segments 11a or clamping elements.

As already mentioned before, the use of the inventive tool-holder is not restricted to medical applications but generally results in improvements in such cases where a tool-holder for a rotatable tool has to be coupled to a rod. Thus, the construction according to the invention could also be used in other motor elements, in particular in high frequency motor spindles or similar elements.

The invention claimed is:

1. A motor element comprising:
   an elongated shank;
   a drive shaft rotatably mounted in the elongated shank;
   a longitundinally-extending rod mounted in the drive shaft and coaxially displaceable within the drive shaft, the longitudinally-extending rod having an open front end proximate a front end region of the elongated shank, and a rear end;
   a tool-holder, at least one end of the tool-holder being disposed within the open front end of the longitudinally-extending rod;
   a disconnectable coupling disposed between the longitudinally-extending rod and the tool-holder;
   a locking element for the coupling that prevents the coupling from disconnecting the tool-holder from the longitudinally-extending rod when a tool is inserted into the tool-holder;
   an actuating sleeve mounted in an annular groove in the elongated shank and located near the rear end of the longitudinally-extending rod; and
   an axially movable pressure element located aft of the rear end of the longitudinally-extending rod, the axially movable pressure element being connected to the actuating sleeve,
   wherein locking/unlocking of the tool-holder and the longitudinally-extending rod is effected by a relative movement between the tool-holder and the tool, and wherein rotation of the actuating sleeve moves the pressure element forward, toward the rear end of the longitudinally-extending rod, thereby moving the longitudinally-extending rod forward, unlocking the coupling.

2. The motor element according to claim 1, wherein the relative movement is a displacement in the longitudinal direction of the longitudinally-extending rod in such a way that the coupling is locked when a tool is located in its working position and is unlocked when the tool is removed.

3. The motor element according to claim 1, wherein the drive shaft, at least in its front end region, is a sleeve and the tool-holder can be plugged into the sleeve.

4. The motor element according to claim 3, wherein the coupling is arranged in the sleeve, and the tool-holder has a plug hole into which the tool can be plugged as far as the region of the coupling.

5. The motor element according to claim 4, wherein a radially movable first coupling element is disposed on the tool-holder and can be moved between a coupling position, where the first coupling element is axially engaged behind a second coupling element disposed on the longitudinally-extending rod, and a position of release in which the first coupling element is disengaged from the second coupling element.

6. The motor element according to claim 5, wherein the first coupling element is biased into the coupling position by the force of a spring.

7. The motor element according to claim 6, wherein the first coupling element is arranged on a spring arm that extends substantially axially.

8. The motor element according to claim 5, wherein the first coupling element is arranged on a rear region of the tool-holder.

9. The motor element according to claim 1, wherein the locking element is held in a coupled position by a tool shank of the tool.

10. A motor element comprising:
    an elongated shank;
    a drive shaft rotatably mounted in the elongated shank;
    a longitundinally-extending rod mounted in the drive shaft and coaxially displaceable within the drive shaft;
    a tool-holder, at least one end of the tool-holder being disposed within an open end of the longitudinally-extending rod;
    a disconnectable coupling disposed between the longitudinally-extending rod and the tool-holder; and
    a locking element for the coupling that prevents the coupling from disconnecting the tool-holder from the longitudinally-extending rod when a tool is inserted into the tool-holder,
    wherein
    locking/unlocking of the tool-holder and the longitudinally-extending rod is effected by a relative movement between the tool-holder and the tool,
    the drive shaft, at least in its front end region, is a sleeve and the tool-holder can be plugged into the sleeve,
    the coupling is arranged in the sleeve, and the tool-holder has a plug hole into which the tool can be plugged as far as the region of the coupling,
    a radially movable first coupling element is disposed on the tool-holder and can be moved between a coupling position, where the first coupling element is axially engaged behind a second coupling element disposed on the longitudinally-extending rod, and a position of release in which the first coupling element is disengaged from the second coupling element, and
    arranged at the front and/or rear ends of the first coupling element and/or second coupling element are oblique or rounded lead-in faces and/or lead-out faces respectively that give rise to automatic yielding of the first coupling element when the tool is drawn out from the tool-holder.

11. The motor element according to claim 10, wherein the lead-in faces and/or lead-out faces are S-shaped.

12. A motor element comprising:
    an elongated shank;
    a drive shaft rotatably mounted in the elongated shank;
    a longitundinally-extending rod mounted in the drive shaft and coaxially displaceable within the drive shaft;
    a tool-holder, at least one end of the tool-holder being disposed within an open end of the longitudinally-extending rod;
    a disconnectable coupling disposed between the longitudinally-extending rod and the tool-holder; and
    a locking element for the coupling that prevents the coupling from disconnecting the tool-holder from the longitudinally-extending rod when a tool is inserted into the tool-holder,
    wherein
    locking/unlocking of the tool-holder and the longitudinally-extending rod is effected by a relative movement between the tool-holder and the tool,
    the drive shaft, at least in its front end region, is a sleeve and the tool-holder can be plugged into the sleeve, and the tool-holder is formed by a collet chuck having a plurality of clamping segments that are arranged so that the clamping segments are distributed over a periphery of the collet chuck and are separated by first longitudinal slots, which open out on an end side, in the associated end region of the collet chuck, with the collet chuck having second longitudinal slots that are staggered in a peripheral direction and open out at another end of the collet chuck and that delimit segments of the collet chuck arranged in between, with the first and the second longitudinal slots overlapping each other in the region of their facing ends.

13. The motor element according to claim 12, wherein at least one of the segments of the collet chuck forms the first coupling element.

14. The motor element according to claim 12, wherein the first and second longitudinal slots are staggered with respect to each other in the peripheral direction.

15. The motor element according to claim 14, wherein the first and second longitudinal slots overlap each other in a region of their facing ends.

16. A motor element comprising:
an elongated shank;
a drive shaft rotatably mounted in the elongated shank, the drive shaft, at least in a front end region thereof having the form of a sleeve;
a longitudinally-extending rod mounted in the drive shaft and coaxially displaceable within the drive shaft, the longitudinally-extending rod having an open front end proximate a front end region of the elongated shank, and a rear end;
a tool-holder arranged in the open font end of the longitudinally-extending rod, the tool holder having an axial plug hole for a tool;
clamping segments that are formed by longitudinal slots in the tool-holder;
an outer cone face of the tool-holder that cooperates with at least one matching inner cone face of the sleeve to clamp the clamping segments against the tool that has been plugged into the plug hole;
an actuating sleeve mounted in an annular groove in the elongated shank and located near the rear end of the longitudinally-extending rod; and
an axially movable pressure element located aft of the rear end of the longitudinally-extending rod, the axially movable pressure element being connected to the actuating sleeve;
wherein the outer and inner cone faces converge frontwardly, and rotation of the actuating sleeve moves the pressure element forward, thereby moving the longitudinally-extending rod frontwardly to unclamp the tool.

17. The motor element according to claim 16, wherein the tool-holder is connected to the longitudinally-extending rod by a disconnectable coupling.

18. The motor element according to claim 16, wherein the drive shaft is transversely divided behind the inner cone and portions of the drive shaft are connected together by a screw connection.

19. A motor element comprising:
an elongated shank;
a drive shaft rotatably mounted in the elongated shank;
a longitudinally-extending rod mounted in the drive shaft and coaxially displaceable within the drive shaft, the longitudinally-extending rod having an open front end proximate a front end region of the elongated shank, and a rear end;
a tool-holder disposed in the open front end of the longitudinally-extending rod, the tool-holder having a central plug hole and a group of clamping elements, the group of clamping elements is arranged so that the clamping elements are distributed over a periphery of the tool-holder and can be moved towards the central plug hole for a clamping process;
an actuating sleeve mounted in an annular groove in the elongated shank and located near the rear end of the longitudinally-extending rod; and
an axially movable pressure element located aft of the rear end of the longitudinally-extending rod, the axially movable pressure element being connected to the actuating sleeve;
wherein rotation of the actuating sleeve moves the pressure element forward, towards the rear end of the longitudinally-extending rod, thereby moving the longitudinally-extending rod forward, and the tool-holder has two groups of clamping elements that are arranged axially one after the other and can be moved simultaneously towards the central plug hole.

* * * * *